United States Patent [19]

Dubreux et al.

[11] Patent Number: 4,943,654

[45] Date of Patent: Jul. 24, 1990

[54] PROCESS FOR PREPARATION OF α-ACETOXY-α-METHYL-N,N'-DIACETYL MALONAMIDE

[75] Inventors: Bernard Dubreux, Francheville Le Haut; Charles Laviron, Lyons, both of France

[73] Assignee: Produits Chimiques Ugine Kuhlmann, Courbevoie, France

[21] Appl. No.: 819,985

[22] Filed: Jan. 15, 1986

Related U.S. Application Data

[63] Continuation of Ser. No. 728,446, May 1, 1985, abandoned, Continuation of Ser. No. 459,100, Jan. 19, 1983, abandoned.

[30] Foreign Application Priority Data

Feb. 2, 1982 [FR] France ............................ 82 01624

[51] Int. Cl.$^5$ .................. C07C 231/06; C07C 235/88
[52] U.S. Cl. .................................... 560/251; 558/345
[58] Field of Search ....................... 560/251; 558/345

[56] References Cited

FOREIGN PATENT DOCUMENTS 2738975  3/1978  Fed. Rep. of Germany ...... 560/251

OTHER PUBLICATIONS

Calmon et al., Ion Exchangers in Organic and Biochemistry, Interscience Publishers, Inc., N.Y., 1957, pp. 662–663.

Dow Chemical Company, Dowex:: Ion Exchanger, Dow Chemical Company, Midland, Michigan, 1964, pp. 7–8 and 34.

Kressman, I. R. E., Manufacturing Chemist, Nov., 1956, pp. 454–458.

*Primary Examiner*—Vivian Garner
*Attorney, Agent, or Firm*—Brooks Haidt Haffner & Delahunty

[57] ABSTRACT

Process for the preparation of α-acetoxy-α-methyl-N,N'-diacetylmalonamide wherein hydrocyanic acid or a cyanide is reacted in a first step with acetic anhydride and then in a second step the reaction mixture so obtained is treated with acetic acid in the presence of an acid catalyst, wherein the first step is carried out in the presence of a catalyst based on anion exchange resins in which the functional groups are quaternary ammonium or tertiary amine, such α-acetoxy-α-methyl-N,N'-diacetylmalonamides being very useful as activators in bleaching and cleaning compositions which are thus active at lower temperatures.

5 Claims, No Drawings

PROCESS FOR PREPARATION OF α-ACETOXY-α-METHYL-N,N'-DIACETYL MALONAMIDE

This application is a continuation, of application Ser. No. 728,446, filed May 1, 1985 abandoned which is a continuation, of application Ser. No. 459,100, filed Jan. 19, 1983 abandoned.

BACKGROUND OF THE INVENTION

The present invention relates to processes for the preparation of diacetylmalonamides, and more particularly, it relates to a high yield process for the production of α-acetoxy-α-methyl-N,N'-diacetylmalonamide in good yields.

α-Acetoxy-α-methyl-N,N'-diacetylmalonamide is a persalt activator having uses in bleaching or cleaning compositions, compositions thus active at lower temperatures. This compound and a method for its preparation are described in French Patent 2,363,541. According to this patent, a particularly advantageous synthesis comprises the reaction in a first step of cyanides or of hydrocyanic acid and a basic catalyst on acetic anhydride, followed by treating the reaction mixture thus obtained with acetic acid in the presence of an acid catalyst. It would be desirable to improve the yield from the first step in the foregoing reaction.

THE INVENTION

It has been discovered according to the present invention that it is possible to carry out synthesis of the α-acetoxy-α-methyl-N,N'-diacetylmalonamide more economically by improving the yield of the first step by carrying out this first step continuously in the presence of catalysts based on anion exchange resins. The present invention accordingly provides a process for preparing α-acetoxy-α-methyl-N,N'-diacetylmalonamide in which there is reacted in a first step a compound which is hydrocyanic acid or a cyanide with acetic anhydride and then, in a second step, treating the mixture so obtained with acetic acid in the presence of an acid catalyst, wherein the first step is carried out in the presence of a catalyst based on anion exchange resins in which the functional groups are quaternary ammonium groups or tertiary amine groups.

The catalysts used according to this invention are all anion exchange resins having functional groups which are quaternary ammonium or tertiary amine. For example, these groups can be benzyldimethylamine or benzyltrimethylammonium carried in the interstitial structure of polymers such as, for example, copolymers of styrene and divinylbenzene.

To carry out the process, a solution of hydrocyanic acid in acetic anhydride is introduced in a tubular reactor containing the resin impregnated with acetic acid and in which the functional groups are in the form of the acetate of tertiary ammonium or of quaternary ammonium.

The molar ratio of acetic anhydride to the hydrocyanic acid can be varied over a large range, but for reasons of yield, it is preferable that the ratio be from about 1 to about 1.2.

The temperature at which the reaction is carried out can be from 20° to about 100° C. In certain preferred embodiments, the reaction is carried out from about 60° to about 90° C.

Unless otherwise stated, all parts, percentages, proportions, and ratios herein are by weight.

The following Examples are given to illustrate embodiments of the invention as it is presently preferred to practice it. It will be understood that these Examples are illustrative, and the invention is not to be considered as restricted thereto except as indicated in the appended claims.

EXAMPLES I AND II

The reactor used is comprised of a 1200 mm long tube having a 10 mm diameter and being helically wound, having a mean diameter of 80 mm. The helix is entirely filled with the stated ion exchange resin in ammonium acetate form, and the helix is immersed in a thermostatic bath.

A pump is used to introduce into this reactor a homogeneous mixture comprising 19.3% hydrocyanic acid and 80.7% acetic anhydride. After the steady state has been reached, 100 g of the liquor leaving the reactor is removed and over a period of 30 minutes is run into an agitated reactor maintained at 50° C. and containing 30 g of glacial acetic acid and 7.5 ml of 70° Baumé sulfuric acid. After two hours at 50° C., the precipitated α-acetoxy-α-methyl-N,N'-diacetylmalonamide is filtered, washed with 100 ml of water, and dried.

In Table I below, the final product yields, calculated with respect to the quantity of hydrocyanic acid and the quantity of potential final product formed at the end of this first step, are shown with respect to the dwell time and per liter of reactor volume according to the present invention and according to the aforesaid French Patent 2,363,541.

TABLE I

| | Example I | Example II | Comparison to French Patent 2,363,541 |
|---|---|---|---|
| Catalyst | Lewatit MP 500 resin (Bayer) | Lewatit MP 62 resin (Bayer) | Triethylamine |
| Temperature | 60° C. | 60° C. | 50° C. |
| Yield based on HCN | 85% | 86% | 84% |
| Amount of final product per hour of dwell and liter of reactor volume | 532 g | 540 g | 87 g |

What is claimed is:

1. A process for the preparation of α-acetoxy-α-methyl-N,N'-diacetylmalonamide in which hydrocyanic acid or cyanide is reacted with acetic anhydride in a first step and then the mixture so obtained is treated with acetic acid in the presence of an acid catalyst in the second step, wherein the first step is carried out with the acetic anhydride in the presence of an anion exchange resin catalyst, wherein the functional groups are the acetate form of quaternary ammonium or tertiary amine groups and the molar ratio of anhydride to hydrocyanic acid or cyanide is at least one.

2. A process according to claim 1 wherein the temperature of the first step of the reaction is from 20° to about 100° C.

3. A process according to claim 1 wherein the reaction temperature is from about 60° to about 90° C.

4. A process according to claim 1 wherein the groups are the acetate form of benzyldimethylamine or benzyltrimethylammonium.

5. A process according to claim 1 wherein the first step is carried out continuously in a tubular reaction zone, the zone being packed with the anion exchange resin.

* * * * *